United States Patent [19]

Martineau et al.

[11] Patent Number: 5,045,460
[45] Date of Patent: Sep. 3, 1991

[54] DNA SEQUENCE ENCODING METALLOCARBOXYPEPTIDASE INHIBITOR PROTEIN

[75] Inventors: Belinda M. Martineau; Kevin E. McBride, both of Davis, Calif.

[73] Assignee: Calgene, Inc., Davis, Calif.

[21] Appl. No.: 365,950

[22] Filed: Jun. 13, 1989

Related U.S. Application Data

[63] Continuation-in-part of Ser. No. 364,362, Jun. 9, 1989.

[51] Int. Cl.$^5$ ..................... C12N 15/09; C12N 15/11; C12N 15/29
[52] U.S. Cl. ..................... 435/172.3; 435/317.1; 536/27; 935/30; 935/67
[58] Field of Search ............ 536/27; 435/172.3, 317.1; 935/30, 35, 64, 67

[56] References Cited

PUBLICATIONS

Hollander-Czytko et al. (1985), Plant Physiology 78: 76–79.
Hilder et al. (1987), Nature 330: 160–163.
Wallace et al. in Methods in Enzymology 152, Berger et al., eds., Academic Press; N.Y., 1987, pp. 432–442.
Sargent, ibid, pp. 423–432.
Helfman et al., ibid, pp. 451–457.
Graham et al. (1981), Biochem. Biophys. Research Commun. 101: 1164–1170.
Pearce et al. (1983), Proceedings of the Society For Experimental Biology and Medicine 173: 447–453.
Ryan (1973), Ann. Rev. Plant Physiol. 24: 173–196.
Hass et al. (1981), Biochemistry 20: 2256–2260.
Bevan et al. (1985) EMBO Journal 4: 1921–1926.
Ryan, C. A.; The Biochemistry of Plants, 1981, 6: 351–370.
Haas et al., Biochemistry, 1975; vol. 14, No. 6, pp. 1334–1342.
Haas and Ryan, Methods in Enzymology, 1981, 80:778–791.
Bishop et al., Journal of Biological Chemistry, 1984; vol. 259, No. 21, pp. 13172–13177.
Pearce and Ryan (b), Analytical Biochemistry, 1983; 130:223–225.
Graham et al., Planta, 1986; 169:399–405.
Green and Ryan, Science, 1971; 175:776–777.
Haas and Ryan, Phytochemistry, 1980; 19:1329–1333.
Broadway et al., Entomol. Exp. Appl.; 1986, 41:33–38.
Ryan et al. (a), Journal of Biological Chemistry; 1974, vol. 249, No. 17, pp. 5495–5499.
Ryan et al. (b), Bayer-Symposium V "Proteinase Inhibitors", 1974; 565–573.
Sambrook et al., "Using Antibodies in Immunological Screening," *Molecular Cloning: A Laboratory Manual*, Second Edition (1989), pp. 12.11–12.15.
Sambrook et al., "Synthesis of cDNA Probes," *Molecular Cloning: Laboratory Manual*, Second Edition (1989), pp. 10.38–10.43.

*Primary Examiner*—Elizabeth C. Weimar
*Assistant Examiner*—Che S. Chereskin
*Attorney, Agent, or Firm*—Elizabeth Lassen

[57] ABSTRACT

In accordance with the subject invention, novel DNA sequences, heterologous constructs and plant expression vectors are provided which relate to the metallocarboxypeptidase inhibitor (MCPI) protein. MCPI protein is capable of inactivating metallocarboxypeptidase, exopeptidase-type digestive enzymes. In addition, this application relates to plant cells and plant entities, including whole plants, plant seed, and plant parts, containing such constructs and methods of providing transgenic plants capable of inhibiting metallocarboxypeptidase (MCP) proteinases and methods of using such for the tolerence of MCPI sensitive pests.

14 Claims, 6 Drawing Sheets

```
     StyI
     SecI
         NlaIII
     NcoI
     DsaI       TspEI     HphI                       BbvI              Fnu4HI
      |          |         |                          |                  |
 1 GATTATTATTACCATGGCACAAAAATTACTATCCTTTTCACCATTCTCCTTGTGGTTATTGCTGCTCA  69
   AspTyrTyrHisGlyThrLysIleTyrTyrProPheHisHisSerProCysGlyTyrCysCysSer
   IleIleIleThrMETAlaGlnLysPheThrIleLeuPheThrIleLeuLeuValValIleAlaAlaGl
   LeuLeuLeuProTrpHisLysAsnLeuLeuSerPheSerProPheSerLeuTrpLeuLeuLeuLeuL
    13        24        32                          50                  64
    13
     17
    13
    13

MboI
                                                          DpnI    Tsp45I
                                                  BinI    BsrI    MaeIII
                                                   |      | |       |
70 AGATGTGATGGCACAAGATGCAACTCTGACGAAACTTTTCAGCAATATGATCCAGTTGTCACAAACC 138
   ArgCysAspGlyThrArgCysAsnSerAspGluThrPheSerAlaIle . SerSerLeuSerGlnThr
   ArgValMETAlaGlnAspAlaThrLeuThrLysLeuPheGlnLysLeuPheGlnLeuPheHisLysPr
   nAspValMETAlaGlnAspAlaThrLeuThrLysLeuPheGlnLeuTyrAspProValCysHisLysPr
   ysMET  .  TrpHisLysMETGlnLeu  .  ArgAsnPheSerAsnMETIleGlnPheValThrAsnL
     77                              114    121    123   129
   SfaNI                                          119           129
    |
```

FIGURE 1
Page 1 of 5

```
                                    StuI
                                    MnlI
                                    HaeIII              FnuDII
                  RsaI               HaeI EcoNI          FinI
           MmeI                      CviJI                AflIII
              MaeII                    |                    |
               ||                      |                    |
139 TTGCTCAACACAAGACGATTGTTCTGGTGGTACGTTCTGTCAGGCCTGTTGGAGGTTCCGCGGGACATG 207
    LeuLeuAsnThrArgArgLeuPheTrpTrpTyrValLeuSerGlyLeuLeuGluValArgGlyAspMET
    oCysSerThrGlnAspAspCysSerGlyGlyThrPheCysGlnAlaCysTrpArgPheAlaGlyThrCy
    euAlaGlnHisLysThrIleValLeuValValArgSerValArgProValGlyGlySerArgGlyHisV
                                                                      204
                171                                200
             168        183  188                198
           170        183
                      183
                      183
```

FIGURE 1
Page 2 of 5

```
        SduI
        NlaIV
   NlaIII           StyI
        HgiJII      SecI         NlaIII
        HaeIII                   NcoI HaeIII
        DraII                    HhaI HaeI
        CviJI              HhaI CfrI
        AsuI    End        FnuDII CviJI
        AsuI         BsePI DsaI BalI
   NspI ApaI         | | |       | | |
   | | | | |         | | |
208 TGGGCCCTATGTTGGGCGCGCCATGGCCATAGGCCGTGTGATTACAATTCGTTGTTCTTCTTTTCGAC 276
    TrpAlaLeuCysTrpAlaArgHisGlyHisGlyArgValIleThrIleSerLeuPhePhePhePheAsp
    sGlyProTyrValGlyArgAlaMETAlaIleGlyVal . LeuGlnPheArgCysSerSerPheSerTh
    alGlyProMETLeuGlyAlaProTrpPro . AlaCysAspTyrAsnPheValValLeuPheArgL
208 214   223 226 229 234                           252              273
    210   226 229 232
    211   228 229 234
    212   229     234
    211           234
    212           233
    214   229
208           229
    212
    214
```

TspEI
                                                 MboII         TaqI
                                                   —            —

256

FIGURE 1
Page 3 of 5

```
277 TTTTAATCCCAAGTGAATAAAGTCTAATTCGAAAAGAAGAAGAAAAAGTATCTATGTCTGAGTTATATG 345
    PheLeuIleProSerGlu . SerLeuIleArgLysArgArgLysLysTyrLeuCysLeuSerTyrMET
    rPhe . SerGlnValAsnLysVal . PheGluLysGluGluLysSerIleTyrVal . ValIleCy
    euPheAsnProLys . IleLysSerAsnSerLysLysLysLysLysValSerMETSerGluLeuTyrV
                            281                          307        327        335
                                                         307
                                                         303
       MseI                    TspEI
                               TaqI          MboII    DdeI
                               AsuII

346 TTTTGTGGCTAATAAGAAATCGACTATGCTTGTTGATTGATAAAATTATGTCATTAGGGTGTGATAT 414
    PheCysGly . GluIleAspTyrAlaCys . PheAspLysAsnTyrValIleArgVal . Tyr
    sPheValAlaAsnLysLysSerThrMETLeuValAspLeuIleLysIleMETSerLeuGlyCysAspME
    aLeuTrpLeuIleArgAsnArgLeuCysLeuLeuIle . LysLeuCysHis . GlyValIleC
                                      354                    366              391
                                                             363
       CviJI          TspEI
                Tth111I
                TaqI
```

FIGURE 1
Page 4 of 5

```
                                                                  TspEI
                                                                  MseI
                                                                   — —
415 GTAATCATCAATTAAATAAAAATCATCGCATTGTGTGTGC 455
    ValIleIleLysLeuAsnLysAsnHisArgIleValCys
    T . SerSerAsn . IleLysIleIleAlaLeuCysVal
    ysAsnHisGlnIleLys . LysSerSerHisCysValCys
                    428
                425
```

FIGURE 1
Page 5 of 5

Carboxypeptidase Inhibitor
(Tomato)

AQDATLTKLFQQYDPVCHKPCSTQDDCSGGTFCQACWRFAGTCGPYVGRAMAIG
::::::::::::::::::::::::::::::::::::
QQYDPVCHKPCSTQDDCSGGTFCQACWRFAGTCGPYV

Carboxypeptidase Inhibitor
(Potato)

AQDATLTKLFQQYDPVCHKPCSTQDDCSGGTFCQACWRFAGTCGPYVGRAMAIG
:: :: ::: :: :::::: :: ::::::::
QQHADPICNKPCKTHDDCSGAWFCQACWNSARTCGPYVG

FIGURE, 2

DNA SEQUENCE ENCODING METALLOCARBOXYPEPTIDASE INHIBITOR PROTEIN

CROSS-REFERENCE TO RELATED APPLICATIONS

This application is a continuation-in-part of U.S. application ser. no. 364,362, filed June 9, 1989, which application is hereby incorporated herein by reference.

FIELD OF THE INVENTION

The present invention concerns novel DNA sequences and their use in genetic engineering of plants for animal and microbial tolerance, especially insects.

BACKGROUND

The application of recombinant DNA technology to plants offers the opportunity to develop new agricultural and plant resources. One goal of plant genetic engineering is the improvement of plant pest protection characteristics, specifically the tolerance of plants to insect pests. Genetically enhanced plant pest tolerance may provide healthier plants, better crop Yields and/or reduce the need for externally applied chemicals.

With respect to the foregoing, DNA sequences which encode inhibitors of animal and microbial digestive enzymes are of interest for genetic engineering applications. Particularly of interest are those DNA sequences which encode potential broad spectrum insect tolerance activity and which will not adversely affect normal plant development and metabolism.

Of special interest herein is the metallocarboxypeptidase inhibitor (MCPI) protein. MCPI is a proteinase inhibitor which abolishes the activity of metallocarboxypeptidases. Metallocarboxypeptidases are exopeptidase-type proteinases which have been found in many animals and microbes, but not in plants.

DESCRIPTION OF RELEVANT LITERATURE

The amino acid sequence of tomato (*Lycopersicon esculentum*) MCPI and potato (*Solanum tuberosum*) MCPI proteins have been published. Hass, et. al., *Biochem.* (1981) 20:2256-2260; Haas, et. al. *Biochem.* (1975) 14:1334-1342.

Other references of interest include: Ryan, Ann. *Rev. Plant Physiol.* (1973) 24: 173-196; Chapter 9, *The Biochemistry of Plants* (1981) Academic Press; Pearce, et al., *Proc. Soc. Exp. Bio. & Med.* (1983) 173:447-453.

SUMMARY OF THE INVENTION

Novel DNA sequences are provided which relate to the cDNA sequence encoding metallocarboxypeptidase inhibitor (MCPI) protein, transgenic plants, heterologous constructs, and plant expression vectors containing same, as well as methods of providing transgenic plants capable of expressing MCPI protein, and methods of protecting against MCPI-susceptible animal and microbial pests by providing transgenic plants capable of inhibiting metallocarboxypeptidase digestive enzymes. The isolation and characterization of the MCPI DNA sequence allows transfer of MCPI protection to plant species which do not naturally have this property, provides the means to enhance MCPI protection in plants which naturally carry the gene, and allows for the manipulation of qualitative (temporal and spacial) and quantitative expression of MCPI for maximization of the pest protective qualities in the recipient genetically engineered plants.

BRIEF DESCRIPTION OF THE DRAWINGS

FIG. 1 shows the complete DNA sequence of a MCPI cDNA clone isolated from tomato and provides the corresponding translated amino acid sequence.

FIG. 2 shows a comparison between the protein sequence of the metallocarboxypeptidase inhibitor of tomato and potato as compared to a translation of the cDNA sequence of tomato MCPI cDNA.

DETAILED DESCRIPTION OF THE INVENTION

In accordance with the subject invention, novel DNA sequences, heterologous constructs and plant expression vectors are provided which relate to the carboxypeptidase inhibitor (MCPI) protein. MCPI protein is capable of inactivating metallocarboxypeptidase (MCP), exopeptidase-type digestive enzymes. In addition, this application relates to plant cells and plant entities, including whole plants, plant seed, and plant parts, containing such constructs and methods of providing transgenic plants capable of inhibiting MCP proteinases and methods of using such for the tolerance of MCPI sensitive pests.

The ability to introduce and/or enhance MCPI protein activity in plants offers the opportunity to provide such plants with the ability to tolerate microbial and animal plant attacks from MCPI-susceptible organisms. Plant hosts of interest include tomato, pea, tobacco, maize, potato, soybean, *Brassica*, cotton, wheat, alfalfa, turf grass, and the like.

"Tolerance" as referred herein relates to the ability to destroy, control or modify the behavior of or shorten the lifespan of an organism or population of organisms by plant hosts with enhanced MCPI production. Because MCPI is delivered though a plant part, the plant pest must ingest a certain amount of the proteinase inhibitor. Ideally, the plant is only moderately damaged before the protective effects of the MCPI protein are realized. Tolerance may include "pesticidal effects" such as death or retarded growth rate of the plant pest organism, especially to prevent an organism from successfully reproducing, rendering the organism more susceptible to other predators or disease, and/or repellent effects, such as learned responses by the organism(s) to avoid the plant host target.

MCPI susceptible plant pests include organisms which rely upon metallocarboxypeptidases in digestion. By this invention, the natural action of required exopeptidase-type digestive enzymes of a MCPI-susceptible attacking plant pest will be reduced and/or abolished rendering the organism(s) unable to secure nutrition from ingested food. In this manner, the growth of the organism may be reduced or slowed, and upon ingestion of toxic levels of MCPI, death from starvation will result. In some instances, it may be desirable to combine MCPI activity with other plant pest genetic tolerance characteristics, such as genes encoding other protease inhibitors or pest toxins for example, to broaden the range of protection of a given plant host against a particular plant pest of interest or to provide tolerance characteristics against a wider range of plant pests. Other protease inhibitors, i.e., non-MCPI inhibitors, include endo-peptidase inhibitors (such as the trypsin inhibitor gene isolated from cowpea as described in European Patent Application 84350393.5 (Publication No. 0135343)) cysteine proteinase inhibitors, amino peptidase inhibitors, and carboxypeptidase inhibitors having different specificity than the MCPI proteinase. Toxins, such as the crystal protein of *Bacillus thuringiensis* (Bt) have been expressed in plants and have shown insecticidal activity (See, European Patent Application 0193259).

MCPI has shown inhibitory activity against mammalian pancreatic carboxypeptidases A & B and other metallocarboxypeptidases from organs or fluids of other animals and microorganisms. See, Haas & Ryan, "Carboxypeptidase inhibitors from potato" in: Lorand, L., ed, *Methods in Enzymology*, New York, Academic Press, Vol. 80:778–(1982). By this invention, it has now been found that naturally occurring MCPI present in one plant species can exhibit a toxicity towards insect pests. In some applications, it may be desirable to apply MCPI externally to plants, either directly or in the vicinity of the plants or plant parts to be protected from insect pests. Of special interest, is the control of insect pests such as *Heliothis* (e.g., *Heliothis virescens* (tobacco budworm), *Heliothis armigera* and *Heliothis zea*). A detailed listing of many agriculturally important insect pests and other plant hosts of interest are found in EPA 84350393.5 (Publication No. 0135343). In that MCPI is effective against a wide range of organisms, it is very likely to be effective against a wide range of insect pests as well. Instar larvae of some insect species appear particularly susceptible to MCPI poisoning, such as *Heliothis virescens*. Deterrence of larvae, especially young larvae, is most preferred because relatively small amounts of the plant must be ingested to realize toxic effects of the proteinase inhibitor. Most preferred is pesticidal activity against first instar larvae The complete cDNA sequence of a MCPI protein and the corresponding translated amino acid sequence is shown in FIG. 1. The plant MCPI sequence may be isolated from plants such as tomato and potato. As shown in FIG. 2, the tomato and potato amino acid sequences show significant homology. From the given sequence, one skilled in the art will be able to determine other analogous MCPI DNA sequences, such as the genomic sequence of the tomato MCPI and other sources of MCPI DNA (cDNA and genomic sequences).

For example, cDNA libraries may be prepared from the plant source of interest, and probes used to identify cDNA sequences for the MCPI gene. The probes can be considerably shorter than the entire sequence, but should be at least about 10, preferably at least about 15, more preferably at least about 20 nucleotides in length. Longer oligonucleotides are also useful, up to the full length of the gene encoding the MCPI protein. Both DNA and RNA probes can be used. The probes can then be used the identify cDNA MCPI sequences in a cDNA library.

Conveniently, the target cDNA may be cloned in a virus, so that hybridizing phage may be plaque-purified. The identified cDNA's may be further sub-cloned and the sub-clone sequence analyzed for the production of probes. Alternatively, commercially available kits may be used for sub-cloning procedures (Lambda Zap, Stratagene). Thus the cDNA can be used to identify genomic sequences in a plant genomic library of the appropriate plant species and the positive clones analyzed by restriction enzyme digestion.

The probes are typically labelled in a detectable manner (for example with $^{32}P$-labelled or biotinylated nucleotides) and used to identify clones from a cDNA or genomic library made from the organism in which a gene is being sought. Typically the clones of the library are plated out and transferred to nitro cellulose or nylon filters which bind nucleic acids. The DNA is denatured on the filters, neutralized and hybridized with the labelled probe. Excess label is washed away and hybridizing clones are detected by means of the label. Hybridization techniques suitable for use with oligonucleotides are well known to those skilled in the art.

Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

Any DNA sequence hybridizable to the mature sequence shown in FIG. I, or fragment thereof, at an appropriate level of stringency and encoding a protein capable of substantially inhibiting the activity of pancreatic carboxypeptidases A or B, is considered within the scope of this invention regardless of source. This includes DNA sequences derived from prokaryotes, eukaryotes (including but not limited to plant sources) and sequences partially or completely synthetically derived. Usually such sequences will have at least about 60%, preferably at least about 70%, identity of base pairs, excluding any deletions which may be present.

It is noted that the complete cDNA includes sequences encoding amino acids not found in the mature MCPI protein. These "pre-processing" sequences may be useful for the proper intra- or intercellular targeting of MCPI. These sequences may be needed to realize the useful properties of the protein, such as targeting of MCPI to plant vacuoles or proper folding, for example. It is preferred that the DNA sequence of MCPI protein engineered into a plant host carry "pre-processing" sequences, i.e. encode precursor protein.

The MCPI DNA sequences, cDNA and/or genomic, of this invention may be used in a variety of forms. In one embodiment, a MCPI DNA is joined to a heterologous DNA sequence. The term "heterologous" refers herein to any sequence not naturally found joined together. Thus it refers to any MCPI construct containing other than wild-type sequences.

At each stage of the preparation of the construct, the resulting product may be cloned and analyzed to insure that the desired product has been obtained. Cloning vectors conveniently will have one or more markers, which will allow for detection of transformants which contain the construct and marker. For the most part, markers will provide for toxin resistance or impart prototrophy to an auxotropic host. Toxin resistance for the most part will be antibiotic resistance, such as resistance to kanamycin and its analogs, e.g. G418, resistance to chloramphenicol, ampicillin, and the like. For the most part, cloning will be performed in *E. coli*, so that a replication system functional in *E. coli* will be employed.

In preparing the constructs of this invention, the various DNA fragments may be manipulated, so as to provide for the sequences in the proper orientation and, as appropriate, in the proper reading frame. Toward this end, adapters or linkers may be employed for joining the DNA fragments or other manipulations may be involved to provide convenient restriction sites, removal of superfluous DNA, removal of restriction sites, or the like. For this purpose, in vitro mutagenesis, primer repair, restriction, annealing, resection, ligation, or the like may be employed, where insertions, deletions, or substitutions (e.g., transitions and transversions) may be involved.

By appropriate manipulations, such as restriction, chewing back or filling in overhangs to provide blunt ends, ligation of linkers, or the like, complementary ends of the fragments can be provided for joining and ligation.

In a preferred embodiment, a construct containing a MCPI DNA of this invention will be found in an expression cassette. By expression cassette is meant that the construct is capable of expressing MCPI when integrated into the genome of a plant host. The expression cassette may be introduced into the plant host genome by many means, such as electroporation, acceleration of DNA particles, protoplast fusion, microinjection, *Agrobacterium tumefaciens* mediated introduction, and the like. The targets for introduction of the DNA may be tissue, particularly leaf tissue with *A. tumefaciens*, disseminated cells, protoplast, seed, embryo, meristematic regions, cotyledons, hypocotyls, pollen, etc. With *A. tumefaciens* introduction, the construct will be further modified by having one or both T-DNA borders present, particularly the right border and the deletion of oncogenes. The construct may be introduced into *A. tumefaciens* carrying the vir genes, where the T-DNA bordered expression construct will be introduced into plant cells infected with *A. tumefaciens*. Techniques exist for the transformation of many dicot and monocot plant species. The means of introduction is not critical to this invention.

An expression construct of this invention will comprise, in the 5' to 3' direction of transcription, a promoter functional in plants and being different from the native promoter of MCPI protein, a MCPI DNA sequence and a transcriptional termination region functional in plants.

The term "promoter" as referred herein are the DNA sequences upstream, sometimes referred to as "5'", to a structural gene involved in inducing the start of transcription and to binding the mRNA to the ribosome.

In this invention, the use of a high expression, "constitutive" (expressed throughout the plant) promoter is preferred. The 35S CaMV promoter, "double 35S CaMV," or 35S enhanced mas promoter (U.S. Pat. Application No. 740,928) are examples. The 35S CaMV is preferred. Less preferred are promoters which are dependent upon wounding for stimulation. However, wound-enhanced promoters, i.e., promoters which are constitutively expressed and which show an increased expression response after wounding, are acceptable. For some applications, promoters which "target" expression in particular plant tissues or at specific timing may be of interest. One purpose could be to offer higher levels of expression in the tissue most susceptible to the plant pest, such as tender, rapidly dividing tissue. An example of a meristematic promoter is elongation factor 1α, "EF-1" described in pending U.S. patent application Ser. No. 234,187.

At the 3' terminus of the structural gene will be provided a termination region which is functional in plants. A wide variety of termination regions are available that may be obtained from genes capable of expression in plant hosts, e.g., bacterial, opine, viral, and plant genes. Suitable transcript termination regions known to those skilled in the art include the nos 3', tml 3', or acp 3', for example.

Once the cells are transformed, transgenic cells may be selected by means of a marker associated with the expression construct. The expression construct will usually be joined with a marker which will allow for selection of transformed plants, as against those cells which are not transformed. The marker will usually provide resistance to an antibiotic, which antibiotic is toxic to plant cells at moderate concentration.

After transformation, the plant cells may be grown in an appropriate medium. In the case of protoplasts, the cell wall will be allowed to reform under appropriate osmotic conditions. In the case of seeds, pollen or embryos, an appropriate germination or callus initiation medium typically would be employed. For explants, an appropriate regeneration medium typically would be used.

Resulting plantlets will be planted and allowed to grow to seed. During the growth, tissue may be harvested and screened for the presence of expression of the expression construct. After growth, the seed may be collected and replanted, or prior to seed formation, the modified plant may be used for fertilizing a different strain or vice versa, so as to provide for a hybrid plant. One or more generations may then be grown to establish that the gene is inherited in Mendelian fashion.

Of particular interest is the cDNA sequence of the MCPI Protein associated with tomato, which has the amino acid and DNA sequence found in the experimental section.

The invention now being generally described, it will be more readily understood by reference to the following examples, which are included for purposes of illustration only and are not intended to limit the invention unless so stated.

EXPERIMENTAL

Expression Vectors

The complete cDNA sequence of tomato MCPI is synthesized, or recovered by use of a probe, derived from the sequence provided in FIG. I, and cloned into the EcoRI site of Stratagene's Bluescript vector (pBluescript II SK-, Stratagene, CA) and clones are selected having the cDNA in the proper orientation (SmaI restriction site at the 5' and SstI restriction site at the 3' end of the cDNA with respect to the direction of the coding sequence) resulting in pZ70. pZ70 is digested with SstI and EcoRV, and the 0.5 kb fragment having the MCPI gene is inserted into SmaI - SstI digested pCGN986 resulting in pCGN2552. pCGN986, described in further detail below, is a 5.6 kb expression cassette in an ampicillin resistant vector backbone and containing a 35SCaMV promoter and a tml 3' region separated by various restriction sites for cloning.

pCGN2552 is digested with HindIII - KpnI to yield an approximately 3 kb fragment which is inserted into the respective HindIII - KpnI digested sites of the binary plasmids pCGN1547 and pCGN1548 yielding 2553 "b" and "a" respectively. pCGN1547 and pCGN1548 (described in greater detail below) contain the same vector backbone (gentamycin resistance) and selectable markers (mas 5'-Kan-mas 3') but contain cloning sites adjacent to its *A. tumefaciens* right border in a different order. Thus, the constructions pCGN2553 "a" and "b" differ in the orientation of the nptII and MCPI gene regions in relation to each other. pCGN2553a, which results from pCGN1548 and pCGN2552, has a head to tail orientation (">>"); pCGN2553b, which results from pCNG1547 and pCGN2552, has a head to head orientation of the two gene regions ("><").

pCGN986 pCGN986 contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMv region VI 3'-end. The CaMV 35S promoter is cloned as an AluI fragment (bp 7144–7734) (Gardner et al., *Nucl. Acids Res.* (1981) 9:2871–2888) into the HincII site of M13mp7 (Messing et al., *Nucl. Acids Res.* (1981) 9:309–321) to create C614. An EcoRI digest of C614 produces the EcoRI fragment from C614 containing the 35S promoter which may be cloned into the EcoRI site of pUC8 (Vieira and Messing, *Gene* (1982) 19:259) to produce pCGN147.

pCGN148a containing a promoter region, selectable marker (KAN with 2 ATG initiator codons) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct pCGN528, is made as follows: pCGN525 is made by digesting a plasmid containing Tn5 which harbors a kanamycin gene (also referred to as "Kan" or "ADPH" II herein) Jorgenson et al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 is made by inserting the BamHI fragment 19 of pTiA6 (Thomashow et al., *Cell* (1980) 19:729–739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMB9KanXXI is a pUC4K variant (Vieira and Messing, *Gene* (1982) 19:259–268) which has the XhoI site missing, but contains a functional kanamycin gene from Tn903 to allow for efficient selection in *Agrobacterium*.

pCGN149a is digested with HindIII and BAMHI and ligated to pUC8 digested with HindIII and BamHI to produce pCGN169. This removes the Tn903 kanamycin marker. pCGN565 and pCGN169 are both digested with HindIII and Pst1 and ligated to form pCGN203, a plasmid containing the CaMV 35S promoter and part of the 5'-end of the TN5 kanamycin gene (up to the PstI site, Jorgenson et al., (1979), supra). A 3'-regulatory region is added to pCGN203 from pCGN204 (an EcoRI fragment of CaMV (bp 408–6105) containing the region VI 3' cloned into pUC18 (Gardner et al., (1981), supra) by digestion with HindIII and Pst1 and ligation. The resulting cassette, pCGN206, is the basis for the construction of pCGN986.

pCGN1547 & pCGN1548 pCGN1547 and pCGN1548 are binary plant transformation vectors containing the left and right T-DNA borders of *Agrobacterium tumefaciens* octopine Ti-plasmid pTiA6 (Currier and Nester. *J. Bact.* (1976) 126:157–165), the gentamycin resistance gene of pPH1JI (Hirsch and Beringer. *Plasmid* (1984) 12:139–141), an *Agrobacterium rhizogenes* Ri plasmid origin of replication from pLJbB11 (Jouanin et al., *Mol. Gen. Genet.* (1985) 201:370–374), the mas promoter region and mas 3' region of pTiA6 with the kanamycin resistance gene of Tn5 (Jorgensen et al., *Mol. Gen. Genet.* (1979) 177:65), a ColE1 origin of replication from pBR322 (Bolivar et al. *Gene* 2:95–113), and a lacZ' screenable marker gene from pUC18 (Yannisch-Perron et al., *Gene* 33:103–119). The backbone of pCGN1547 and pCGN1548, containing the gentamycin resistance gene and the pRi and ColE1 origins, is derived from pCGN1532 (see below). The T-DNA borders and plant selectable marker gene (mas5'-kan-mas3') for pCGN1547 and pCGN1548, as well as the multiple cloning site and screenable marker (lacZ'), are from pCGN1543(see below) and pCGN1544(see below), respectively; the plant selectable marker cassette is taken from pCGN1536, while the right border:lacZ':left border cassette fragments are derived from pCGN1541b (see below) and pCGN1542b(see below), respectively.

A. pCGN1532 construction.

The 3.5kb EcoRI-PstI fragment containing the gentamycin resistance gene is removed from pPH1JI (Hirsch and Beringer (1984) supra) by EcoRI-PstI digestion and cloned into EcoRI-PstI digested pUC9 to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al (1977) supra) to create pBR322Gm. pBR322Gm is digested with DraI and SphI, treated with Klenow enzyme to create blunt ends, and the 2.8 kb fragment cloned into the Ri origin-containing plasmid pLJbB11 (Jouanin et al. (1985), supra) which has been digested with ApaI and made blunt ended with Klenow enzyme, creating pLJbB11Gm. The extra ColE1 origin and the kanamycin resistance gene are deleted from pLJbB11Gm by digestion with BamHI followed by self closure to create pGmB11. The HindIII site of pGmB11 is deleted by HindIII digestion followed by treatment with Klenow enzyme and self closure, creating pGmB11-H The PstI site of pGmB11-H is deleted by PstI digestion followed by treatment with Klenow enzyme and self closure, creating pCGN1532.

B. pCGN1536 construction.

The 5.4 kb EcoRI fragment was removed from pVK232 (Knauf and Nester, *Plasmid* (1982) 8:45–54) by EcoRI digestion and cloned into EcoRI digested pACYC184 (Chang and Cohen. *J. Bact.* (1978) 134:1141–1156) to create pCGN14. The 1434 bp ClaI-SphI fragment of pCGN14, containing the mas 5' region (bp 20128–21562 according to numbering of Barker, et al., (*Plant Mol Biol.* (1983) 2:335–350), is cloned into AccI-SohI digested pUC19 (Yanisch-Perron, et al., *Gene* (1985) 53:103–119) to generate pCGN40. A 746 bp EcoRV-NaeI fragment of the mas 5' region is replaced by an XhoI site by digesting pCGN40 with EcoRv and NaeI followed by ligation in the presence of a synthetic XhoI linker DNA to create pCGN1036. The 765 bp SstI-HindIII fragment (bp 18474-19239) of pCGN14, containing the mas 3' region, is cloned into SstI-HindIII digested pUC18 (Yanisch-Perron, et al., Gene (1985) 53:103-119) to yield pCGN43. The HindIII site of pCGN43 is replaced with an EcoRI site by digestion with HindIII, blunt ending with Klenow enzyme, and ligation of synthetic EcoRI linker DNA to create pCGN1034. The 767 bp EcoRI fragment of pCGN1034 is cloned into EcoRI digested pCGN1036 in the orientation that placed bp 19239 of the mas 3' region proximal to the mas 5' region to create pCGN1040. pCGN1040 is subjected to partial digestion with SstI, treated with T4 DNA polymerase to create blunt ends, and ligated in the presence of synthetic XhoI linker DNA; a clone was selected in which only the SstI site at the junction of bp 18474 and vector DNA (created in pCGN43 and carried into pCGN1040) is replaced by an XhoI site to generate pCGN1047.

pCGN565 (a cloning vector based on pUC8-pUC13-cm (K. Buckley, Ph.D., Thesis UC San Diego (1985)) but containing pUC18 linkers (Yanisch-Perron, et al., Gene (1985) 53:103-119) is digested with EcoRI and HindIII, treated with Klenow enzyme to create blunt ends, and ligated in the presence of synthetic XhoI linker DNA to create pCGN1003; this recreates the EcoRI site adjacent to the XhoI linker. pCGN1003 is digested with EcoRI, treated with Klenow enzyme to create blunt ends, and ligated in the presence of synthetic PstI linker DNA to create pCGN1007. The 1.5 kb XhoI fragment of pCGN1047, containing the mas 5' region and the mas 3' region with a multiple cloning site between, is cloned into XhoI digested pCGN1007 to create pCGN1052. A portion of the multiple cloning site of pCGN1052 is deleted by digestion with XbaI and SstI, treated with Klenow enzyme to make blunt ends, and ligated to generate pCGN1052DXS.

The 1 kb EcoRI-SmaI fragment of pCGN550 (The HindIII-SmaI fragment of Tn5 containing the entire structural gene for kanamycin (Jorgensen, et al., Mol. Gen. Genet. (1979) 177:65) is cloned into HindIII-SmaI digested pUC8 (Vieira and Messing, Gene (1982) 12:259-268). This converts the fragment into a HindIII-EcoRI fragment, since there is an EcoRI site immediately adjacent to the SmaI site. pCGN300 contains a BglII-SalI fragment of TN5 having kanamycin resistance in a BamHI-SalI digested pUC backbone. The PstI-EcoRI fragment of pCGN300, containing the 3'-portion of the kanamycin gene, is then combined with an EcoRI-BamHI-SalI-PstI linker into the EcoRI site of pUC7 to make pCGN546W. An ATG codon is upstream from and out of reading frame with the ATG initiation codon of APH3'II, the kanamycin gene. The undesired ATG is avoided by inserting a Sau3A-PstI fragment from the 5'-end of APH3'II, which fragment lacks the superfluous ATG, into the BamHI-PstI site of pCGN546W to provide plasmid pCGN550)), containing the 1 ATG-kanamycin resistance gene, and is then cloned into EcoRI-SmaI digested Bluescript M13−KS (Strategene, Inc.) to create pBSKm; this plasmid contained an M13 region allowing generation of single stranded DNA. Single stranded DNA is generated according to the supplier's recommendations, and in vitro mutagenesis is performed (Adelman et al., DNA (1983) 2:183-193) using a synthetic oligonucleotide with the sequence 5'GAACTCCAGGACGAGGC3' to alter PstI site within the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1535 is cloned into EcoRI digested pCGN1052DXS to create the mas5'-kan-mas3' plant selectable marker cassette pCGN1536.

C. pCGN1541b and pCGN1542b construction.

pUC18 is digested with HaeII to release the lacZ' fragment, treated with Klenow enzyme to create blunt ends, and the lacZ'-containing fragment ligated into pCGN565RB−H+X which had been digested with AccI and SphI and treated with Klenow enzyme, resulting in pCGN565RBα2X and pCGN565RBαX.

To create pCGN565RB−H+X, pCGN451 was digested with HpaI and ligated in the presence of synthetic SphI linker DNA to generate pCGN55. The XhoI-SphI fragment of pCGN55 (bp13800-15208, including the right border, of Agrobacterium tumefaciens T-DNA; (Barker et al., Gene (1977) 2:95-113) is cloned into SalI-SphI digested pUC19 (Yanisch-Perron et al., Gene (1985) 53:103-119) to create pCGN60. The 1.4 kb HindIII-BamHI fragment of pCGN60 is cloned into HindIII-BamHi digested pSP65 (Promega, Inc.) to generate pCGN1039. pCGN1039 is digested with SmaI and NruI (deleting bp14273-15208; (Barker et al., Gene (1977) 2:95-113) and ligated in the presence of synthetic BglII linker DNA creating pCGN1039ΔNS. The 0.47 kb EcoRI-HindIII fragment of pCGN1039ΔNS is cloned into Eco-RI-HindIII digested pCGN565 (See pCGN1536 description) to create pCGN565RB. The HindIII site of pCGN565RB was replaced with an XhoI site by HindIII digestion, treatment with Klenow enzyme, and ligation in the presence of synthetic XhoI linker DNA to create pCGN565RB−H+X.

In pCGN565RBα2X the orientation of lacZ' is such that the lac promoter is proximal to the right border whereas in pCGN565RBα3X the lac promoter is distal to the right border. Both clones are positive for lacZ' expression when plated on an appropriate host. Each contain bp 13990-14273 of the right border fragment (Barker et al. (1983) supra), having deleted the AccI-SphI fragment (bp (13800-13990). The 728 bp BglII-XhoI fragment of pCGN565RBα2X and pCGN565RBα3X, containing the T-DNA right border piece and the lacZ' gene, are cloned into BglII-XhoI digested pCGN65ΔKX−S+X, replacing the BglII-XhoI right border fragment of pCGN65ΔKX−S+X, to create pCGN65α2X and pCGN65α3X, respectively.

pCGN501 is constructed by cloning a 1.85 kb EcoRI-XhoI fragment of pTiA6 (Currier and Nester, J. Bact. (1976) 126:157-165) containing bases 13362-15208 (Barket et al., Plant Mo Biol. (1983) 2:335-350) of the T-DNA (right border), into EcoRI-SalI digested M13mp9 (Vieira and Messing, Gene (1982) 19:259-268). pCGN502 is constructed by cloning a 1.6 kb HindIII-SmaI fragment of pTiA6, containing bases 602-2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (vieira and Messing, Gene (1982) 19:259-268) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, Gene (1980) 11:291-298) to generate pCGN518. The KpnI-EcoRI fragment from pCGN518, containing the left T-DNA border, is cloned into KpnI-EcoRI digested pCGN565 to generate pCGN580. The BamHI-BglII fragment of pCGN580 is cloned into the BamHI site of pACYC184 (Chang and Cohen, *J. Bacteriol.* (1978) 134:1141-1156) to create pCGN51. The 1.4 kb BamHI-SphI fragment of pCGN60 (See pCGN565RB−H+H above) containing the T-DNA right border fragment, is cloned into BamHI-SphI digested pCGN51 to create pCGN65.

pCGN65 is digested with KpnI and XbaI, treated with Klenow enzyme to create blunt ends, and ligated in the presence of synthetic BglII linker DNA to create pCGN65ΔKX. pCGN65ΔKX is digested with SalI, treated with Klenow enzyme to create blunt ends, and ligated in the presence of synthetic XhoI linker DNA to create pCGN65ΔKX−S+X. The 728 bp BglII-XhoI fragment of pCGNRBx2X, containing the T-DNA right border piece and the lacZ' gene, is cloned into BglII-XhoI digested pCGN65ΔKX−S+X, replacing pCGN65x2X. The ClaI fragment pCGN65x2X is deleted and replaced with an XhoI linker by digesting with ClaI, treating with Klenow enzyme to create blunt ends, and ligating in the presence of synthetic XhoI linker DNA to create pCGN65Δ2XX.

The ClaI fragment from both pCGN65α2X and pCGN65α3X is deleted and replaced with an XhoI linker by digesting with ClaI, treating with Klenow enzyme to create blunt ends, and ligating in the presence of synthetic XhoI linker DNA to create pCGN65α2XX and pCGN65α3XX, respectively. pCGN65α2XX and pCGN65α3XX are each digested with BglII and EcoRV, treated with Klenow polymerase to generate blunt ends, and BglII linkers added. The resulting plasmids, pCGN65α2XX' and pCGN65α3XX', now each lack an approximately 20 bp piece of DNA present in the parent plasmids which carries spurrious BamHI and EcoRV restriction sites.

pBR322 is digested with EcoRI and PvuII, treated with Klenow polymerase to generate blunt ends, and BglII linkers added. An ampicillin resistant, tetracycline sensitive clone, pCGN1538 is selected. This clone now lacks the approximately 2.2 kb EcoRI-PvuII fragment containing the tetracycline resistance gene. The PvuII site has been lost but the EcoRI site is regenerated upon addition of BglII linkers.

pCGN65α2XX' and pCGN65α3XX' are digested with BglII and ligated to BglII digested pCGN1538 to create pCGN1541a and pCGN1542a, respectively: each containing both plasmid backbones. pCGN1541a and pCGN1542a are digested with XhoI and religated. Ampicillin resistant, chloramphenical sensitive clones are chosen which lacked the pACYC184 derived backbones, creating pCGN1541b and pCGN1542b, respectively.

D. Construction of pCGN451 pCGN451 contains the ocs5'-ocs3' cassette cloned into a derivative of pUC8 (vieira and Messing, *Gene,* (1982) 19:259-268). The modified vector is derived by digesting pUC8 with HincII and ligating in the presence synthetic linker DNA, creating pCGN416, and then deleting the EcoRI site of pCGN416 by EcoRI digestion followed by treatment with Klenow enzyme and self ligation to create pCGN426.

The ocs5'-ocs3' cassette is created by a series of steps from DNA derived from the octopine Ti-plasmid pTiA6 (Currier and (Nester, *J. Bact.* (1976) 126:157-165). An EcoRI fragment of pTiA6 (bp 13362-16202; the numbering is by Barker, et al., *Plant Mol Biol.* (1983) 2:335-350), for the closely related Ti plasmid pTi15955) is removed from pVK232 (Knauf and Nester, *Plasmid* (1982) 8:45) by EcoRI digestion and cloned into EcoRI digested pACYC184 (Chang and Cohen, *J. Bacteriol.* (1978) 134:1141-1156) to generate pCGN15.

The 2.4kb BamHI-EcoRI fragment (bp 13774-16202) of pCGN15 was cloned into EcoRI-BamHI digested pBR322 (Bolivar, et al., *Gene* (1977) 2:95-113) to yield pCGN429. The 412 bp EcoRI-BamHI fragment (bp 13362-13774) of pCGN15 is cloned into EcoRI-BamHI digested pBR3322 (Bolivar, et al., *Gene* (1977) 2:95-113) to yield pCGN407. The cut-down promoter fragment is obtained by digesting pCGN407 with XmnI (bp 13512), followed by resection with Ba131 exonuclease, ligation of synthetic EcoRI linkers, and digestion with BamHI. Resulting fragments of approximately 130 bp are gel purified and cloned into M13mp9 (Vieira and Messing, *Gene* (1982) 19:259-268) and sequenced. A clone, I−4, in which the EcoRI linker has been inserted at bp 13642 between the transcription initiation point and the translation initiation codon is identified by comparison with the sequence of de Greve, et al., (de Greve, et al., *J. Mol. Appl. Genet.* (1982) 1:499-512). The EcoRI cleavage site is at position 13639, downstream from the mRNA start site. The 141 bp EcoRI-BamHI fragment of I-4, containing the cut-down promoter, is cloned into EcoRI-BamHI digested pBR322 (Bolivar, et al., *Gene* (1977) 2:95-113) to create pCGN428. The 141 bp EcoRI-BamHI promoter piece from pCGN428, and the 2.5 kb EcoRI-BamHI ocs 5' piece from pCGN429 are cloned together into EcoRI digested pUC9 (Vieira and Messing, *Gene* (1982) 19:259-268) to generate pCGN442, reconstructing the ocs upstream region with a cut-down promoter section.

The HindIII fragment of pLB41 (D. Figurski, UC San Diego) containing the gentamycin resistance gene is cloned into HindIII digested pACYC184 (Chang and Cohen, *J. Bacteriol.* (1978) 134:1141-1156) to create pCGN413b. The 4.7 kb BamHI fragment of pTiA6 (Currier and Nester, *J. Bact.* (1976) 126:157-165) containing the ocs 3' region, was cloned into BamHI digested pBR325 (F. Bolivar, *Gene* (1978) 4:121-136) to create 33c-19. The SmaI site a+position 11207 (Barket, et al.) of 33c-19 is converted to an XhoI site using a synthetic XhoI linker, generating pCGN401.2. The 3.8 kb BamHI-EcoRI fragment of pCGN401.2 is cloned into BamHI-EcoRI digested pCGN413b to create pCGN419.

The ocs5'-ocs3' cassette is generated by cloning the 2.64 kb EcoRI fragment of pCGN442, containing the 5' region, into EcoRI digested pCGN419 to create pCGN446. The 3.1 kb XhoI fragment of pCGN446, having the ocs 5' region (bp 13639-15208) and ocs 3' region (bp 11207-12823), are cloned into the XhoI site of pCGN426 to create pCGN451.

E. pCGN1547 and pCGN1548 final assembly.

The XhoI fragment of pCGN1536 containing the mas5'-Kan$^R$-mas3' region is cloned into XhoI digested 1541b and 1542b to create pCGN1543 and pCGN1544, respectively. The XhoI fragment from pCGN1536 is oriented within pCGN1543 such that the order of components is left border-mas5'-Kan$^R$-mas3'-lacZ'>-right border. The T-DNA segment of pCGN1544 is essentially the same as that of
. pCGN1543 except for the orientation of the lacZ' gene.

The T-DNA containing BglII fragments of pCGN1543 and pCGN1544 are cloned into BammHI restricted pCGN1532 resulting in binary vectors, pCGN1547 and pCGN1548, respectively. In both vectors, the orientation of the insert is such that the T-DNA left border is adjacent to the pRi origin of replication. These binary vectors have several advantages including a minimal amount of DNA between the T-DNA borders, high stability in *Agrobacterium* hosts, high copy number in *E. coli* hosts and blue/white screen with multiple restriction enzyme sites for ease of cloning target DNA.

Tobacco Transformation a. Preparation of *A. tumefaciens* pCGN2553a and pCGN2553b are introduced into the disarmed *Agrobacterium* strain LBA4404 by transformation and selection on media containing 100 μg/ml gentamycin. The transformed strains are maintained on AB media (AB salts: $K_2HPO_4$ 3gm/l, $NaH_2PO_4 \cdot H_2O$ 1.15g/l, $NH_4Cl$ 1g/l, glucose 5g/l, $FeSO_4$ 0.25mg/l, $MgSO_4$ 0.246mg/l, 0.14mg/l, 15g/l agar) containing gentamycin and streptomycin.

b. Transformation of Tobacco

The region between the T-DNA borders of pCGN2553a and PCGN2553b are introduced into tobacco (*Nicotiana tabacum* "Xanthi") via *A. tumefaciens* mediated transformation.

Tobacco leaf explants, roughly 5–10mm by 5–10mm, are cut from young leaves, approximately 3–5cm long and third to sixth from the apex which have been grown under axenic conditions in solid medium Murashige Minimal Organics (#1118 Gibco Laboratories, New York), 7% phytagar, 1mg/l indole-3-acetic acid, 0.15mg/l kinetin. The explants are plated on solid medium containing Murashige Minimal Organics, 6% phytagar, 40mg/l adenine sulfate, 2mg/l indole-3-acetic acid, 2mg/l kinetin. A sterile #1 Whatman filter paper (Whatman Ltd., Maidstone, England) is placed on the top of the plate medium (explants are placed on top of filter) and they are incubated for 24 hours in the dark at 24° C.

The *Agrobacterium* containing the binary plasmids are grown on AB medium (AB salts: $K_2HPO_4$ 3gm/l, $NaH_2PO_4 \cdot H_2O$ 15g/l, $NH_4Cl$ 1g/l, glucose 5g/l, $FeSO_4$ 0.25mg/l, $MgSO_4$ 0.246mg/l, 0.14mg/l, 15g/l agar) 100 μg/l gentamycin sulfate and 100 μg/l streptomycin sulfate) for 4–5 days. Single colonies are inoculated into 5mls of MG/L broth (50% Luria broth and 50% mannitol-glutamate salts medium (Garfinkel and Nester, *J. Bacteriol.* (1980)144:732–743)) and are incubated overnight in a shaker at 30° C. and 180 R.P.M. before co-cultivation.

Following the preincubation period, the explants are dipped into the bacterial suspension which has been diluted to $3.3 \times 10^8$ cells/ml with fresh MG/L media for approximately 5 minutes, blotted on sterile paper towels and replated on the same plates. After 48 hours, the explants are placed on selection medium containing the same plate medium as above plus 350mg/l cefotaxime and 100mg/l kanamycin. The explants are transferred to fresh media every 2 weeks. At the 6 week transfer thereafter, shoot and green callus are trimmed from explants and the shoots and green callus are placed on solid media: Murashige Minimal Organics, 0.5mg/l indole-3-acetic acid, 2 mg/l kinetin, 40mg/l adenine sulfate, 350mg/l cefotaxime, 100mg/l kanamycin. Shoots may be harvested beginning about 4 weeks after co-cultivation and placed in 50ml culture tubes with 25ml of solid medium (7% bactagar 1mg/l indole-3-butyric acid, 350mg/l cefotaxime, 100mg/l kanamycin) and grown at 24–28° C., 12 hours light, 12 hours dark, light intensity 80–100 $\mu Em^{-2}s^{-1}$. Shoots root in 1–2 weeks and are then transplanted into soil and placed in growth chambers.

Tobacco Budworm

Feeding Assay

Transformed and non-transformed Xanthi tobacco are grown in a growth chamber for an average of 22 days (range 11 to 32 days) at 28° C., 16 hr days with 400 $\mu E/m^2$/sec light and no humidity control.

Three young leaves are removed from each test plant and approximately 0.2 g of leaf material is placed into five 2 ounce straight sided flint glass bottles w/ 53 mm plastic lids (Northwestern Bottle Co., CA) containing 0.75 ml of 2% water agar (Bacto-Agar, Difco Laboratories, MI). Thus, each plant is tested in five separate events. Four control plants are used for a total of 20 control events.

Tobacco budworm (*Heliothis virescens*) eggs obtained from USDA-ARS Southern Field Crop Insect Management Lab (Stoneville, MS) are hatched in original containers placed in sealed plastic bags at 29° C. with 12 hr days and 25 $\mu E/m^2$/sec. Two first instar larvae are placed on the leaf material of each jar and incubated under the same conditions as egg hatching.

Results

Surprisingly, in plants believed to be successfully transformed, measurable increases in insect mortality are observed as compared with control untransformed plants. Insect mortality is seen at levels up to about 80-100% in some constructs/events as compared with the approximate 50-55% of mortality seen in the controls. Interestingly, pCGN2553b shows the most promising results.

As seen from the above results, MCPI transformed plants show increased insect mortality over the controls. In accordance with the above invention, MCPI can be introduced or enhanced in a plant host for the delivery of pesticidally effective amounts of MCPI.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A cDNA sequence encoding a plant derived metallocarboxypeptidase inhibitor protein.

2. The sequence of claim 1 comprising the sequence shown in FIG. 1.

3. The sequence of claim 1 hybridizable to tomato metallocarboxypeptidase inhibitor protein cDNA.

4. The sequence of claim 1 encoding metallocarboxypeptidase inhibitor precursor protein.

5. A nucleic acid construct comprising a sequence encoding a plant-derived metallocarboxypeptidase inhibitor protein joined to a heterologous sequence.

6. The construct of claim 5 wherein said sequence encoding a metallocarboxypeptidase inhibitor protein is cDNA.

7. The construct of claim 6 wherein said plant is tomato.

8. The construct of claim 5 wherein said sequence encoding a metallocarboxypeptidase inhibitor protein encodes metallocarboxypeptidase inhibitor precursor protein.

9. The construct of claim 5 wherein said construct comprises, in the 5' to 3' direction of transcription, a promoter functional in plants and being different from the native promoter of said sequence encoding a plant derived metallocarboxypeptidase inhibitor; a sequence encoding a plant derived metallocarboxypeptidase inhibitor precursor protein, and a transcriptional termination region functional in plants.

10. The construct of claim 9 wherein said promoter is derived from 35S CaMV.

11. The construct of claim 9 wherein said DNA sequence encoding a plant derived metallocarboxypeptidase inhibitor precursor protein is cDNA.

12. The construct of claim 11 wherein said DNA sequence encoding a plant derived metallocarboxypeptidase inhibitor protein is derived from tomato.

13. A plant expression vector comprising a construct of any one of claim 9, 10, 11, and 12.

14. The sequence of claim 1 wherein said plant is tomato.

* * * * *